(12) United States Patent
Aguren

(10) Patent No.: US 9,610,062 B2
(45) Date of Patent: Apr. 4, 2017

(54) PERIOPERATIVE OCULAR DISTENTION (POD) MONITOR

(71) Applicant: Sperion Medical Devices LLC, Austin, TX (US)

(72) Inventor: Derrick Aguren, Austin, TX (US)

(*) Notice: Subject to any disclaimer, the term of this patent is extended or adjusted under 35 U.S.C. 154(b) by 0 days.

(21) Appl. No.: 15/053,849

(22) Filed: Feb. 25, 2016

(65) Prior Publication Data

US 2016/0249881 A1 Sep. 1, 2016

Related U.S. Application Data

(60) Provisional application No. 62/120,968, filed on Feb. 26, 2015.

(51) Int. Cl.
| | |
|---|---|
| A61B 3/10 | (2006.01) |
| A61B 8/10 | (2006.01) |
| G02B 27/30 | (2006.01) |
| G02B 3/14 | (2006.01) |
| A61B 3/00 | (2006.01) |
| A61B 8/08 | (2006.01) |

(52) U.S. Cl.
CPC ............. *A61B 8/10* (2013.01); *A61B 3/0025* (2013.01); *A61B 3/0041* (2013.01); *A61B 3/10* (2013.01); *A61B 8/485* (2013.01); *G02B 3/14* (2013.01); *G02B 27/30* (2013.01)

(58) Field of Classification Search
USPC ................................................ 351/200–246
See application file for complete search history.

(56) References Cited

U.S. PATENT DOCUMENTS

| | | | |
|---|---|---|---|
| 8,511,825 B2* | 8/2013 | Sander ............... | G02B 21/0012 351/214 |
| 8,639,306 B2* | 1/2014 | Cornsweet ......... | A61B 5/14507 600/318 |

* cited by examiner

*Primary Examiner* — Mohammed Hasan
(74) *Attorney, Agent, or Firm* — Intrinsic Law Corp.

(57) ABSTRACT

Systems and methods for measuring a patient's relative ocular distention as an indicator of eye, brain, and systemic hemodynamic and physiological conditions are provided. Ocular distention is measured and displayed continuously through the closed eyelid by strain imaging techniques, for example with ultrasound or optical computed tomography.

17 Claims, 9 Drawing Sheets

PERIOPERATIVE OCULAR DISTENTION (POD) MONITOR

TECHNICAL FIELD

The present invention is directed to measuring a patient's relative ocular distention as an indicator of eye, brain, and systemic hemodynamic and physiological conditions.

RELATED APPLICATIONS

This application claims the benefit and priority of U.S. Provisional Application No. 62/120,968, filed on Feb. 26, 2015, which is incorporated herein by reference.

BACKGROUND

An acute depression in local perfusion pressure and blood flow is a direct indicator of an increased risk of ischemic damage. Direct, continuous measurement of local blood and other fluidic pressures and flows can therefore be critical in acute situations such as trauma and surgery, but is currently difficult or impossible, particularly in the case of central nervous system (CNS) pressures and flows. Direct, continuous measurement of intracranial pressure (ICP) is currently only available via invasive techniques, while intracranial blood flows are only available indirectly via measurements of velocity using Doppler ultrasound. Intraocular pressure (ICP) and blood flow can be measured noninvasively, but only with the eye open and for short durations.

It would be desirable to have an apparatus to overcome the above deficiencies.

BRIEF DESCRIPTION OF THE DRAWINGS

For a fuller understanding of the nature and advantages of the present invention, reference is be made to the following detailed description of preferred embodiments and in connection with the accompanying drawings, in which.

SUMMARY

Figure 1:
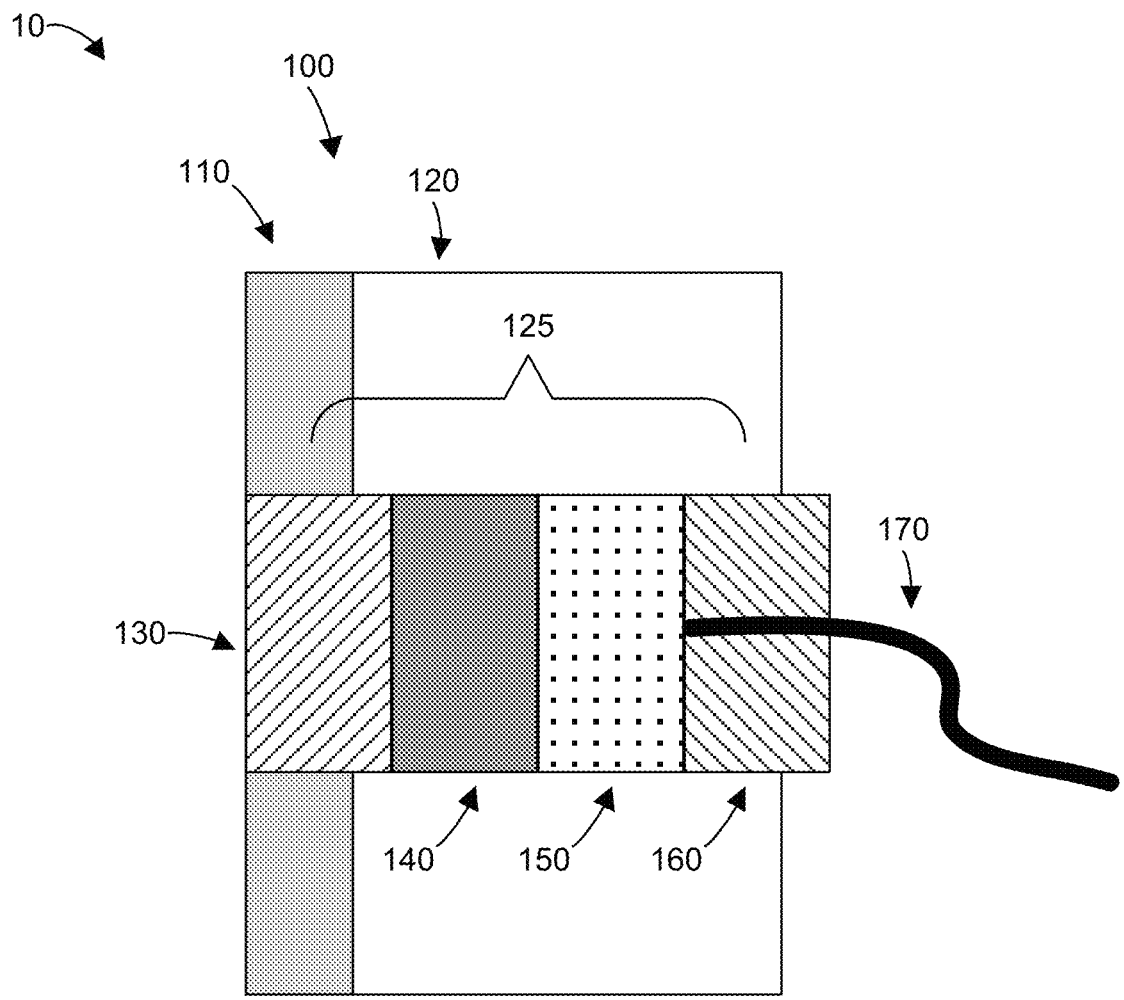
FIG. 1 illustrates a illustrates a side view of a transpalpebral ultrasonic probe assembly according to an embodiment.

To address the foregoing problems, and achieve other advantages, it is presented that a clinically useful substitute for direct measurements of CNS pressures and flows is via continuous, noninvasive monitoring of their volumetric effects on the eye. Continuous perioperative monitoring of ocular distention would give the clinician indications of a variety of otherwise difficult to monitor conditions, including: acute changes in ocular and cerebral perfusion pressures; possible occlusion of a feeder artery to the eye, e.g. ophthalmic or internal carotid; acute changes in eye hemodynamic conditions; changes in eye hemodynamic resistance; changes in eye hemodynamic capacitance; acute changes in intraocular pressure (IOP); occlusion of eye arterial or venous flow; occlusion of aqueous humor outflow; acute changes in intracranial pressure (ICP); changes in intracranial arterial pressure; changes in cerebrospinal fluid (CSF) pressure; exhaustion of the cerebral autoregulatory reserve; changes in blood viscosity; and clinically significant changes in patient orientation and physical support.

Since pressure $P=V/C$ for a container's volume V and capacitance C, changes in the eye's total volume directly indicates changes in the local blood pressure gradient for constant capacitance. Changes in gradient P may be from changes in one or more of arterial, venous, intraocular, or external pressures. Ocular capacitance can be treated as constant during a single cardiac cycle, but may change over a series of cycles due to changes in intraocular fluid volume and arterial muscle tone.

In some embodiments, the present system and method measures changes in eye volume continuously and noninvasively via physical strain of the corneoscleral envelope. This is accomplished by transpalpebral incremental strain imaging using in vivo strain imaging methods such as ultrasound speckle tracking and optical coherence elastography (OCE) via optical coherence tomography (OCT). Incremental strain is the change in local length over original length, where length for the scleral sphere is some circumferential or axial distance. In general, an ultrasonic or laser system probe is applied to the closed eyelid secured for example with a strap, surgical tape, or as a component of an adhesive patch. This probe is driven by an electronic or electro-optical system, respectively, which is also responsible for computing, transmitting, and displaying results as continuous waveforms and trends over time.

In an aspect, the probe does not contact the ocular surface directly and further does not apply pressure to take measurements. This may be accomplished by the imaging system compensating electronically for intervening acoustically or optically visible layers and any oblique orientation to the imaged scleral or corneal surface.

In an aspect, the invention is directed to an apparatus for noninvasive monitoring of an eye. The apparatus includes an adhesive support structure and an ultrasound device. The adhesive support structure includes an elongated flexible backing layer having a first planar surface. The adhesive support structure also includes an adhesive layer disposed on said first planar surface of said elongated flexible backing layer. The ultrasound device is disposed in an aperture defined in said adhesive support structure. The ultrasound device includes a rigid or semi-rigid backing layer. The ultrasound device also includes a driver circuitry disposed on said rigid or semi-rigid backing layer. The ultrasound device also includes an array of ultrasound transducers in electrical communication with said driver circuitry. The ultrasound device also includes a coupling gel disposed on said array of ultrasound transducers.

In another aspect, the invention is directed to an apparatus for noninvasive monitoring of an eye. The apparatus includes an adhesive support structure and an optical device. The adhesive support structure includes an elongated flexible backing layer having a first planar surface. The adhesive support structure also includes an adhesive layer disposed on said first planar surface of said elongated flexible backing layer. The optical device is disposed in an aperture defined in said adhesive support structure. The optical device includes a housing. The optical device also includes a cable including a fiber optic cable and electronic cable as needed connected to a first wall of said housing. The optical device also includes a collimating lens disposed proximal to said first wall of said housing, said collimating lens forming collimated electromagnetic (EM) waves from uncollimated EM waves passing through said collimating lens, said uncollimated EM waves emitted from said fiber optic cable. The optical device also includes a fixed or electronically variable focusing lens disposed proximal to a second wall of said housing, said focusing lens configured to focus said collimated EM waves at a target in said eye. The probe cable, collimating lens, and focusing lens are disposed in said housing.

In another aspect, the invention is directed to a system for noninvasive monitoring of an eye. The system includes a transpalpebral probe assembly including an adhesive support structure and an ultrasound device. The adhesive structure includes an elongated flexible backing layer having a first planar surface. The adhesive structure also includes an adhesive layer disposed on said first planar surface of said elongated flexible backing layer. The ultrasound device is disposed in an aperture defined in said adhesive support structure. The ultrasound device includes a rigid or semi-rigid backing layer. The ultrasound device also includes a driver circuitry disposed on said rigid or semi-rigid backing layer. The ultrasound device also includes an array of ultrasound transducers in electrical communication with said driver circuitry. The ultrasound device also includes a coupling gel disposed on said array of ultrasound transducers. The system also includes a microprocessor-based computer in communication with the assembly. The computer includes a probe driver complex including a driver logic to provide a control signal to said driver circuitry in said ultrasound device and analog-to-digital converters to transform an output of the ultrasound device to digital signals. The computer also includes a processor in communication with the probe driver complex, the processor outputting a signal representing a transpalpebral acoustical image of a portion of a subject's eye based at least in part on the digital signals. The system also includes a display in communication with the computer, the display displaying the image.

In another aspect, the invention is directed to a system for noninvasive monitoring of an eye. The system includes an assembly including an adhesive support structure. The adhesive support structure includes an elongated flexible backing layer having a first planar surface. The adhesive support structure also includes an adhesive layer disposed on said first planar surface of said elongated flexible backing layer. The assembly also includes an optical device disposed in an aperture defined in said adhesive support structure. The optical device includes a housing and a fiber optic cable connected to a first wall of said housing. The optical device also includes a collimating lens disposed proximal to said first wall of said housing, said collimating lens forming collimated electromagnetic (EM) waves from uncollimated EM waves passing through said collimating lens, said uncollimated EM waves emitted from said fiber optic cable. The optical device also includes a focusing lens disposed proximal to a second wall of said housing, said focusing lens configured to focus said collimated EM waves at a target in said eye. The fiber optic cable, said collimating lens, and said focusing lens are disposed in said housing. The system also includes a light source having a coupling in electrical communication with the fiber optic cable. The system also includes a microprocessor-based computer in communication with the assembly and the light source, the computer including a processor to determine a corneal strain of a subject and to generate an output signal representing a transpalpebral optical image of a portion of a subject's eye, the corneal strain and the output signal based at least in part on an output signal of the assembly. The system also includes a display in communication with the computer, the display displaying the image.

DETAILED DESCRIPTION

FIG. 1 illustrates a side view of a transpalpebral ultrasonic probe assembly 10 according to an embodiment. The assembly 10 includes a mounting structure 100 and an ultrasound structure 125. The mounting structure 100 includes an adhesive layer 110 disposed on flexible backing 120. The adhesive layer 110 is integrated into the assembly 10 to adhere the assembly 10 to a patient's eyelid while the assembly 10 is in clinical use. In some embodiment, adhesive layer 110 can include a low trauma adhesive such as a hydrogel, acrylic, silicone, or other adhesive. Alternatively, a cranial strap, headset, surgical tape, or similar device can be used in place of adhesive layer 110 to secure the assembly 10 to a patient's eyelid. Flexible backing 120 secures the ultrasound structure 125 to the eyelid via adhesive layer 110. Flexible backing 120 can include a bandage, a woven fabric, a plastic material (e.g., polyvinyl chloride, polyethylene, polyurethane), or a latex material.

In some embodiments, the mounting structure 100 is similar to an ECG lead. In general, the mounting structure 100 has a form factor (e.g., dimensions) that allow the mounting structure 100 to be mounted on a patient's eye. Exemplary assembly 10 dimensions are about 8 mm wide, about 20 mm long, and about 5 mm thick. However, other dimensions are within the scope of this disclosure, including assembly 10 dimensions of about 6 mm to about 10 mm wide, about 15 mm to about 25 mm long, and about 3 mm to about 7 mm thick. The flexible backing 120 can be about 1 mm to about 2 mm thick or about 1.5 mm thick. The ultrasound structure 125 can be about 2 mm to about 6 mm wide or about 4 mm wide, about 5 mm to about 15 mm long or about 10 mm long, and about 3 mm to about 7 mm thick or about 5 mm thick. As used herein, "about" means plus or minus 10% of the relevant value.

Ultrasound structure 125 is disposed in a central region of mounting assembly 100. Ultrasound structure 125 includes coupling gel 130, ultrasonic transducer elements 140, driver circuitry 150, and rigid backing 160. The driver circuitry 150 receives control signals through cabling 170. The control signals can be generated by an internal or external microprocessor-based controller. The driver circuitry 150 includes electronics to convert the control signals to driver signals to drive an array of ultrasound transducer elements 140. Rigid backing 160 provides support for ultrasound structure 125 and in some embodiments is a hard polymer such as polystyrene. Rigid backing 160 can also be semi-rigid, such as latex, in some embodiments.

In some embodiments, the ultrasound transducer elements 140 include small, lightweight micromachined ultrasonic transducers (MUTs) instead of or in addition to conventional piezoelectric transducers. An example of such MUTs can be found in U.S. Pat. No. 6,359,367, which is incorporated herein by reference. Ultrasound transducer elements 140 can include an array (e.g., a linear array) of ultrasound elements, for example an array of 64 elements.

Coupling gel 130 includes an acoustic coupling medium to transmit acoustic energy generated by transducer elements 140 to the patient (e.g., via the patient's eyelid). Preferred gels are non-toxic and water-soluble, e.g., SCAN Ultrasound Gel from Parker Laboratories, Inc.

In some embodiments, the assembly 10 can include a cover or a removable material to cover the adhesive layer 110 and/or the coupling gel 130 prior to application of the assembly 10 on a subject, for example during storage.

Figure 2:
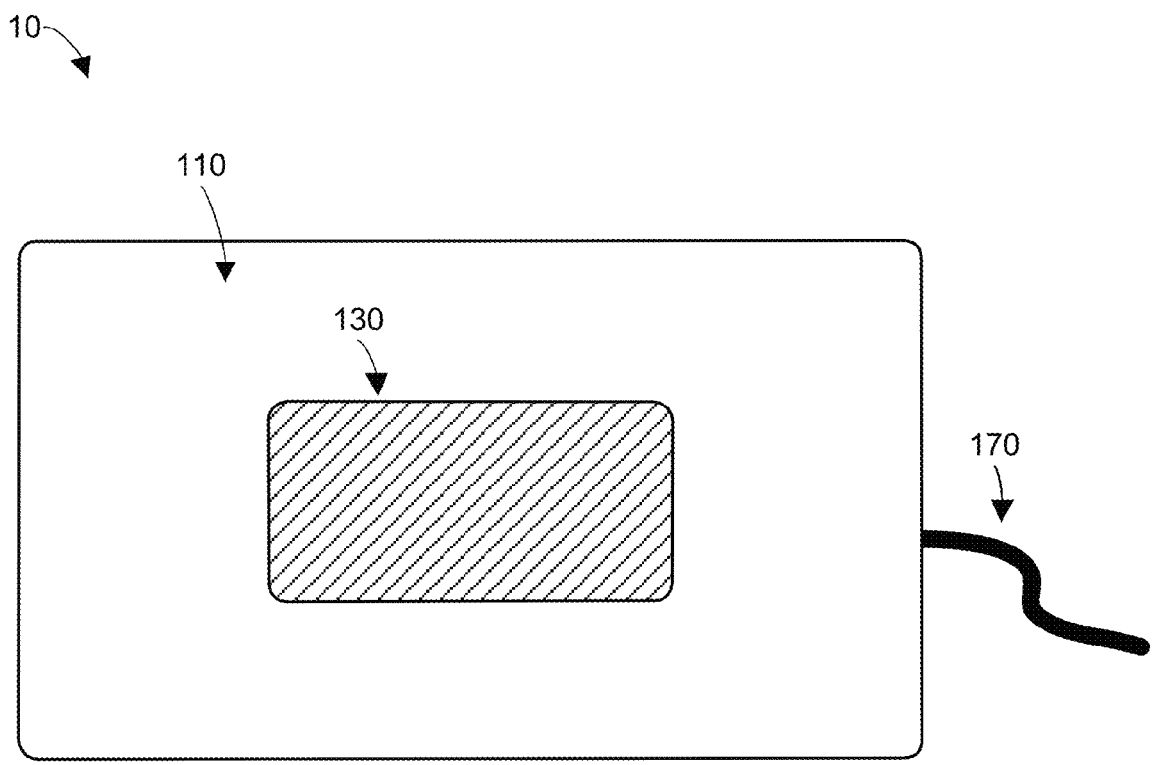
FIG. 2 illustrates a bottom view of the transpalpebral ultrasonic probe assembly of FIG. 1.

FIG. 2 illustrates a bottom view of the transpalpebral ultrasonic probe assembly 10 described above. As can be seen, the coupling gel 130 is generally in the center of the assembly 10. The adhesive layer 110 surrounds the coupling gel and forms the balance of the bottom surface of assembly 10. Cabling 170 is illustrated in FIG. 2 for context, although cabling 170 enters ultrasonic structure 125 from the top of assembly 10. As discussed above, a cover or removable material can cover the adhesive layer 110 and/or the coupling gel 130.

Figure 3:
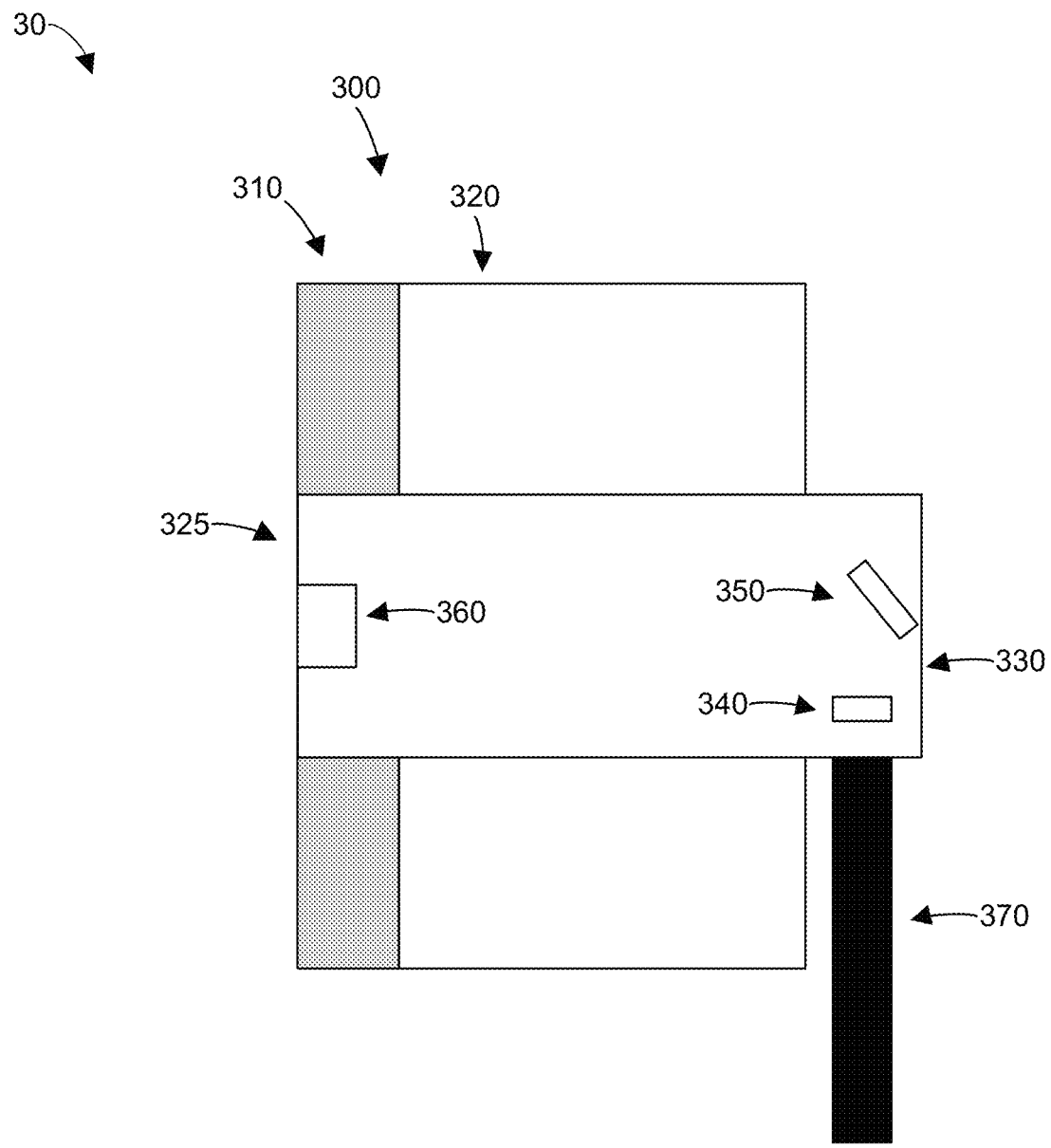
FIG. 3 illustrates a side view of an OCE probe assembly for optical coherence elastography (OCE) according to an embodiment.

FIG. 3 illustrates a side view of an OCE probe assembly 30 for optical coherence elastography (OCE) according to an embodiment. The OCE assembly 30 includes a mounting structure 300 and an optical assembly 325. The mounting structure 300 includes adhesive layer 310 and flexible backing 320, which can be the same as adhesive layer 110 and flexible backing 120 described above.

Optical assembly 325 includes housing 330, collimating lens 340, mirror 350, and focusing lens 360. Housing 330 is illustrated as transparent for clarity, but in some embodiments one or more of the collimating lens 340, mirror 350, and focusing lens 360 are obstructed from view.

In operation, electromagnetic waves (EM waves) (e.g., light) pass through probe cable 370, which can include a fiber optic cable or a fiber optic bundle, and enter housing 330, for example through a window that is transparent to the EM waves. The EM waves then pass through collimating lens 340 where the EM waves are collimated. The collimated EM waves are redirected by mirror 350, which is disposed at an acute or obtuse angle with respect to an axis parallel to the collimated EM waves. The mirror 350 is configured to direct or redirect the EM waves so they pass through focusing lens 360, which focuses the EM waves on a target on the patient's eye and/or on the patient's lower eyelid. In some embodiments, the focusing lens 360 is removable and can be replaced by a lens appropriate for a given patient. In yet another embodiment, lens 360 is an electronically-controlled liquid lens with a dynamic focal point. The probe cable 370 can include an electronic cable to power and drive the electronically-controlled liquid lens. In addition or in the alternative, the clinician can select from several optical probe assemblies 30 or optical assemblies 325, each of which contain a different lens.

The assembly 30 allows a conventional OCT system to be decoupled between the bulky electro-optical/mechanical scanning assembly and the small and lightweight assembly 30.

Figure 4:
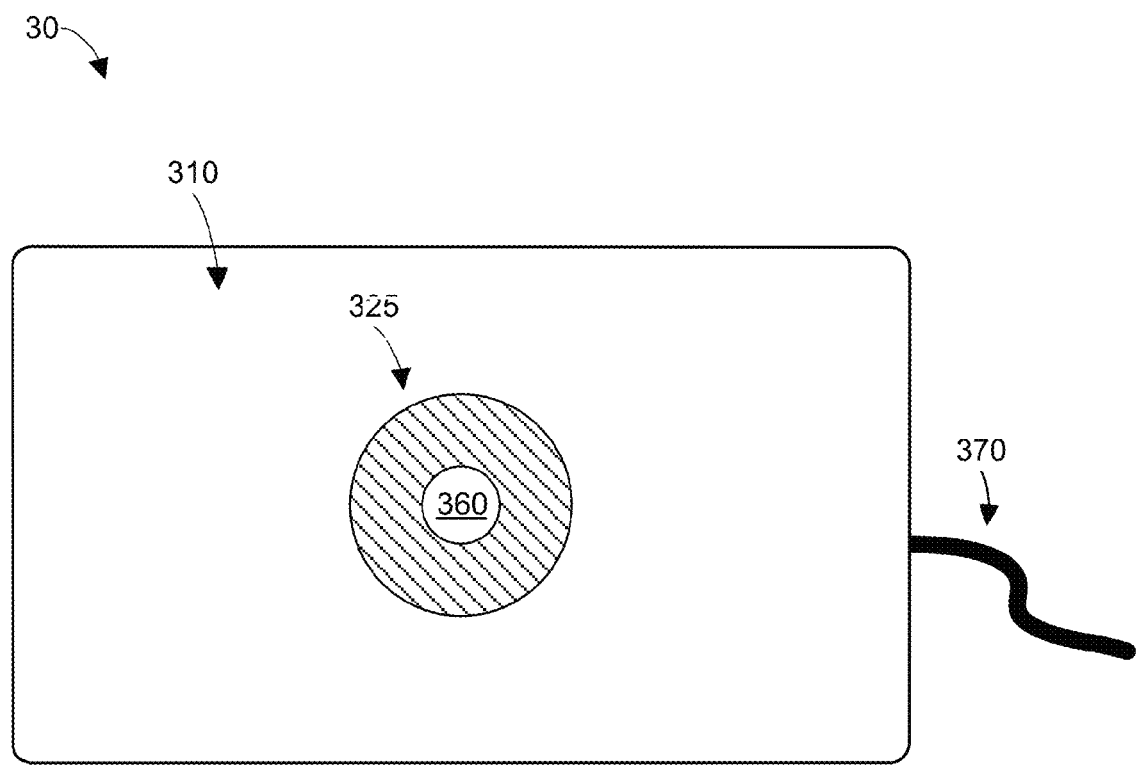
FIG. 4 illustrates a bottom view of the OCE probe assembly of FIG. 3.

FIG. 4 illustrates a bottom view of assembly 30 described above. As can be seen, the optical assembly 325 is generally in the center of the assembly 30. The adhesive layer 310 surrounds the optical assembly 325 and forms the balance of the bottom surface of assembly 30. Probe cable 370 is illustrated in FIG. 4 for context, although probe cable 370 enters optical assembly 325 from the top of assembly 30. As can be seen, the assembly 30 can be applied to a patient in a similar manner as an ECG lead.

Figure 5:
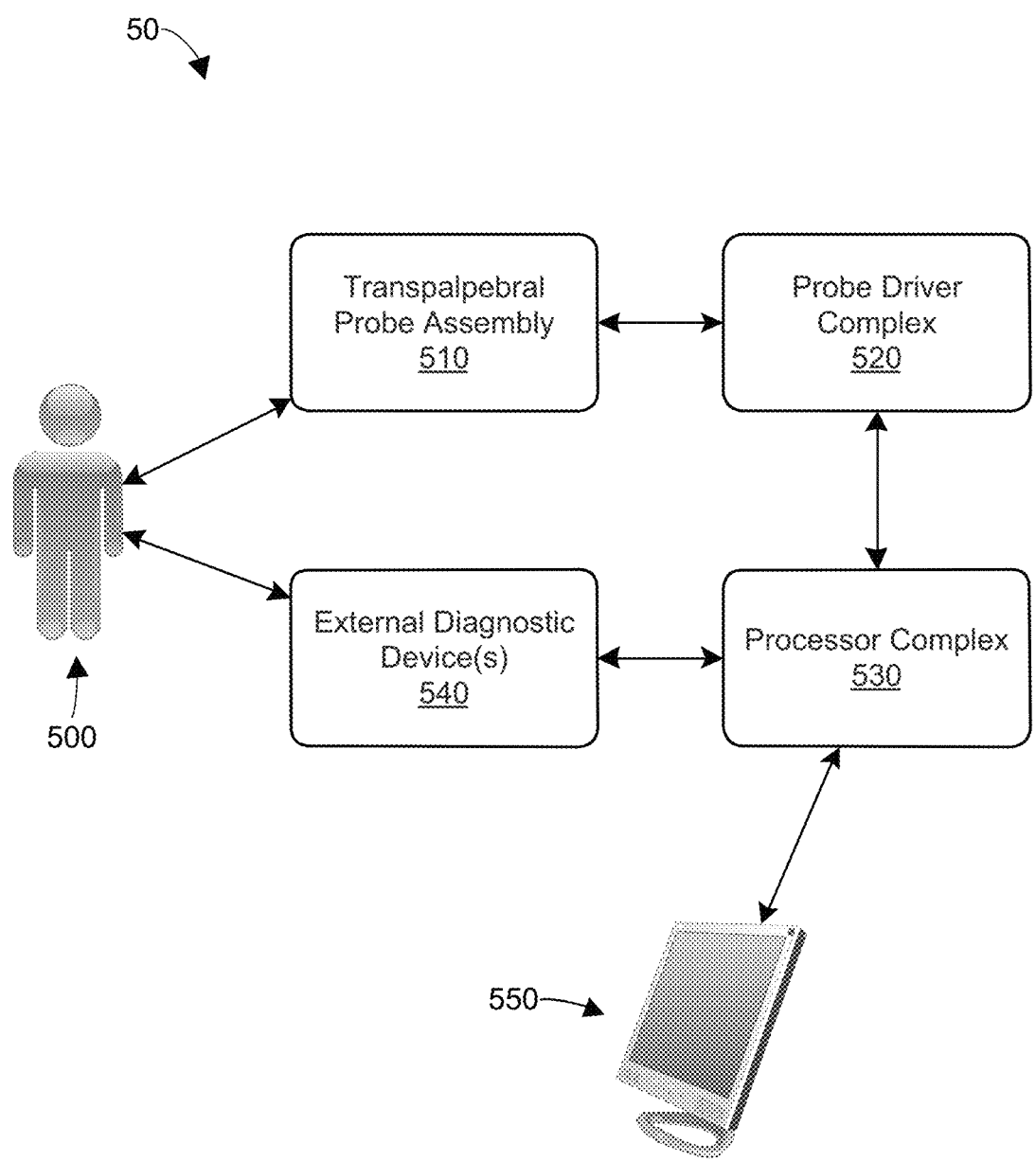
FIG. 5 is a block diagram of a system for transpalpebral incremental strain imaging according to an embodiment.

FIG. 5 is a block diagram of a system 50 for transpalpebral incremental strain imaging according to an embodiment. The system 50 includes transpalpebral probe assembly 510, probe driver complex 520, processor complex 530, external diagnostic device 540, and user interface 550.

The transpalpebral probe assembly 510 can be the transpalpebral ultrasonic probe assembly 10 or the OCE probe assembly 30, as discussed above. The assembly 510 is in electrical communication with probe driver complex 520. Probe driver complex 520 includes components such as an interface to processor complex 530. The interface can be physical or it can be virtualized in software. The probe driver complex 520 includes the components specific to the imaging modality. In some embodiments, the probe driver complex 520 and the processor complex 530 are disposed in the same physical device, such as a computer or a server.

In the case of a typical OCT implementation using a Michelson interferometer and OCE probe assembly 30, the probe driver complex 520 includes a light source, an aiming laser diode, a beamsplitter, a reference arm assembly, a photo-diode with amplifier and local image storage, a scan head and lens system, and a fiber-optic coupling mechanism to the OCE probe assembly 30. The light source can be a broadband super luminescent diode (SLD) and can have a central wavelength of about 800 nm to about 1400 nm at 10 mW output, including about 900 nm, about 1000 nm, about 1100 nm, about 1200 nm, and about 1300 nm, 1310 nm, or any value between any two of the foregoing wavelengths. The bandwidth can be about 50 nm to about 100 nm, including about 60 nm, about 70 nm, about 80 nm, about 90 nm, or any value between any two of the foregoing bandwidths. The reference arm assembly can include a phase modulator, a calibrated scanning mirror, a lens assembly, and associated electronic drivers. Alternatively, the reference arm can be implemented in solid state without any moving parts. An exemplary system is described in U.S. Pat. No. 8,770,755, which is incorporated herein by reference. Scan frames are forwarded to processor complex 530.

In the case of a typical ultrasound strain imaging implementation using transpalpebral ultrasonic probe assembly 10, the probe driver complex 520 includes electronic analog-to-digital converters, digital signal processing filters, local RF and digital image storage, and driver logic. The drive logic can include logic output a control signal for the driver circuitry on the ultrasound device of probe assembly 10. There is typically one analog-to-digital converter for each transducer element in ultrasonic transducer elements 140. Frames can be forwarded to processor complex 530 for speckle tracking and analysis.

Since transpalpebral strain imaging requires a small scan area at only a few millimeters depth, high frequency ultrasound on the order of 10 to 30 MHz can be used to optimize strain measurement accuracy. To provide a continuous waveform, the system further preferentially uses ultrafast B-mode imaging at a high (>1000 Hz) frame rate. One or more embodiments may employ ultrafast B-mode image processing using modern graphics processing platforms for high computational throughput. The ultrasonic frequency, waveforms, and imaging are controlled by the driver logic.

Processor complex 530 is responsible for the computationally intense aspects of image processing, elastography, hemodynamics, external I/O, user control, and results storage and forwarding. In addition, processor complex 530 can implement a speckle-tracking algorithm, e.g. as described in Tang, J. and Liu, J., *Ultrasonic Measurements of Scleral Cross-Sectional Strains During Elevations of Intraocular Pressure: Method Validation and Initial Results in Posterior*

*Porcine Sclera,* Journal of Biomechanical Engineering 2012; 134(9), 091007-1-091007-10, which is incorporated herein by reference. In addition, processor complex 530 can compute the strain (e.g., strain of stromal or corneal tissue) and combine the results of strain with inputs provided by external diagnostic device(s) 540, such as ocular spherical diameter, to compute derivable diagnostic metrics. An exemplary algorithm for optical coherency micro-elastography is presented in Kennedy, B. et al., "Optical Coherence Micro-Elastography: Mechanical-Contrast Imaging of Tissue Microstructure," Biomedical Optics Express, 2014 Jun. 9; 5(7):2113-24, which is incorporated herein by reference. In an additional embodiment, processor complex 530 estimates the nominal total scleral volume from the 3D local images of the sclera via the radius of curvature of the en face segment. The processor complex 530 can provide this information and results to the user through user interface 550. These functions are generally independent of the imaging implementation and are preferentially implemented in software.

Figure 6:
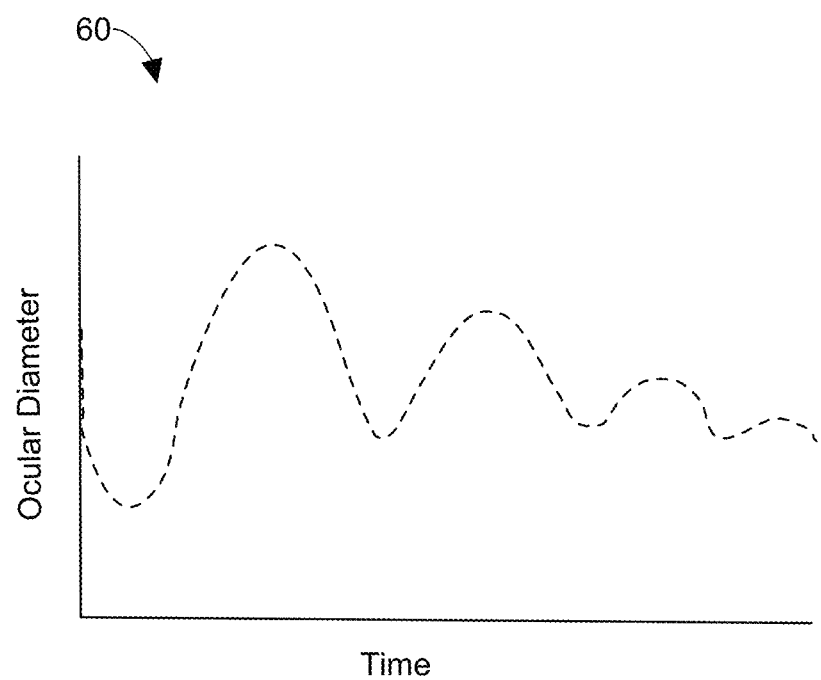
FIG. 6 illustrates an exemplary graph that can be presented to the user according to an embodiment.

User interface 550 can include a touch-screen monitor or a display that can accept menu-driven user input. Such user input can include configuration parameters for probe assembly 510, probe driver complex 520, and/or processor complex 530. User input can also include data obtained from external diagnostic devices 540 or commands to synchronize external diagnostic devices 540 with processor complex 530. User interface 550 also allows the user to display data, waveforms, trends, and other information generated and obtained by processor complex 530. An example of the data that can be provided on user interface 550 is graph 60 illustrated in FIG. 6. As illustrated in the graph 60, the ocular diameter is observed to be decreasing. As ocular diameter is related to strain, the decreasing trend may indicate an acute decrease in retinal and ciliary artery perfusion pressures due to a developing thrombus in the ophthalmic artery.

Continuous intracranial pressure, intraocular pressure, ocular perfusion pressure (OPP), ocular pulse amplitude (OPA), and pulsatile ocular blood flow (POBF) estimates in absolute terms are derived from ocular distention, additional estimates of baseline total volume from the 3D images of the local sclera, and via supplemental data provided by the user and/or external diagnostic devices 540 such as brachial artery blood pressures.

Figure 7:
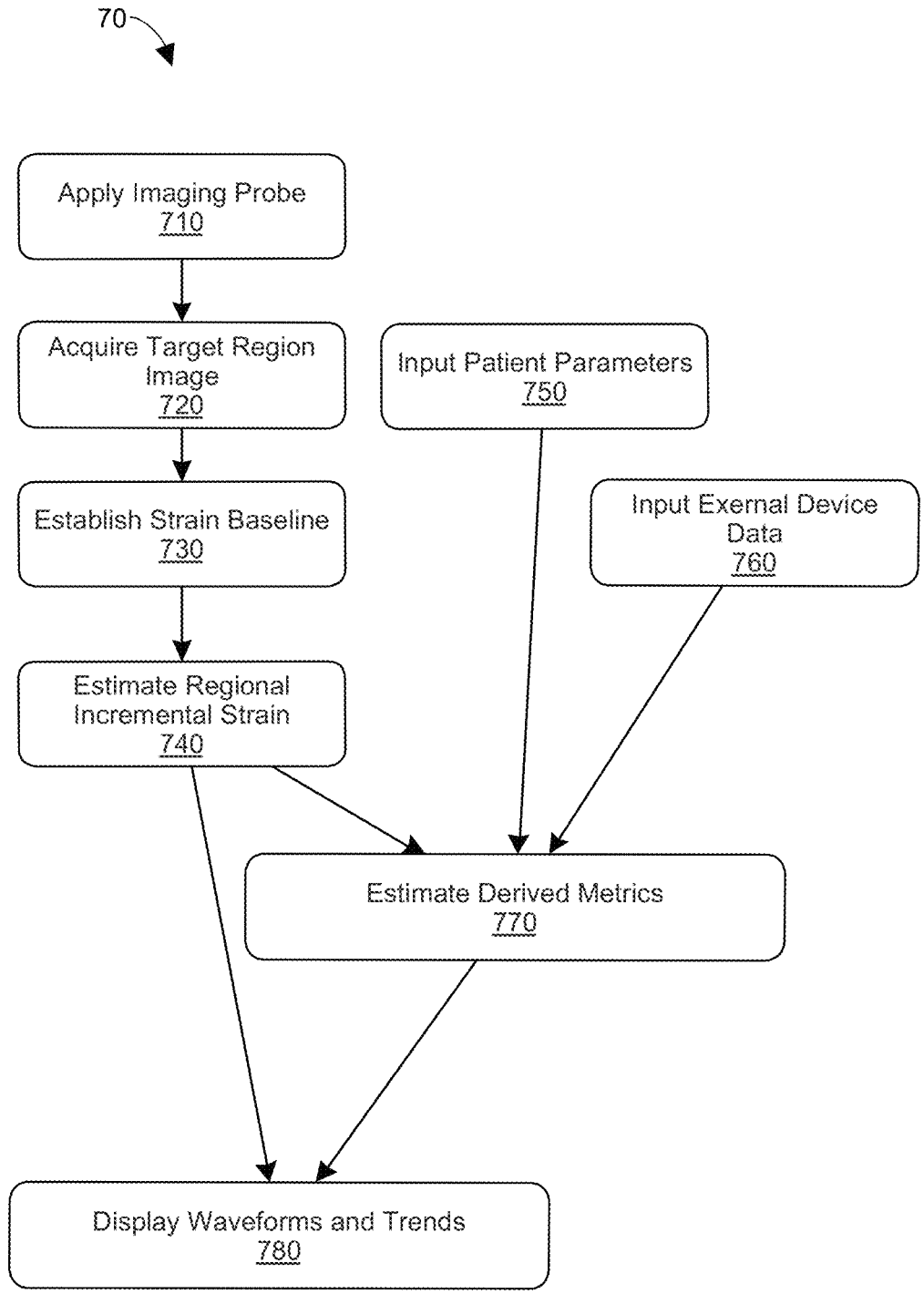
FIG. 7 illustrates a flowchart of a method of acquiring data from a patient according to an embodiment.

FIG. 7 illustrates a flowchart 70 of a method of acquiring data from a patient using system 50 described above. In step 710 ultrasound probe 10 or OCE probe 30 is affixed to the patient's eyelid by the user/clinician. The patient's eyes remain closed for the duration of the measurements. In step 720, an acoustically imaged (using probe 10) or optically imaged (using probe 30) region of the surface or volume of the stroma of either the sclera or cornea of the patient's eye is acquired electronically. Target stromal/corneal tissue is distinguished from intervening layers of acoustically/optically visible tissue and fluids by the relative characteristics and depth of the return signal as compared to empirically-based profiles. For example, in a transpalpebral ultrasound image at 30 MHz, the changes in acoustic impendences between eyelid, conjunctiva, sclera, and the vitreous chamber readily delineate the boundaries those tissues. The speckle densities further distinguish these tissues. For the higher-resolution optical method tissues are similarly readily distinguished by coarse-grained histological features, e.g., cell volumetric density. Modified profiles are input by the user in step 750 for abnormal physiologies or pathologies. As anterior scleral circumferential elastic properties are largely independent of circumferential direction, the array 10, 30 can be oriented at any angle with respect to the closed eyelid seam. Corneal elastic properties are strongly directional, requiring for corneal applications a standard transducer orientation or alternatively an indication to the device of the transducer orientation with respect to the orientation of additionally provided parameters.

In step 730, a zero incremental strain baseline is established. The user signals to the device (e.g., via user interface 550) that the current image represents the strain baseline. In the perioperative context this baseline often corresponds to stable patient conditions. If used, additional baseline data such as absolute intraocular pressure measurements, e.g. with dynamic contour tonometry, and baseline brachial artery pressure are measured and provided to the device at this time. Such additional baseline data is input in step 760.

In step 740, the system continuously estimates, measures, and records regional incremental strain. Total incremental strain relative to the eye baseline geometry can be estimated as the product of the series of incremental strain measurements.

In step 750, the user inputs patient parameters to the system, e.g., through user interface 550. Patient parameters can include ocular rigidity and ocular diameter. Such parameters can be used to estimate certain diagnostic metrics that are dependent on measured ocular distention. For example, the parameters can be used to estimate scleral meridional diameter, absolute IOP, and pulsatile ocular blood flow. Alternatively, the system can provide empirical estimates of these values from provided patient parameters such as age and gender.

In step 760, the external device data is input into the system. The data can be input manually by the user or automatically by a device through a physical or wireless connection with the external device. An example of external device data that may be beneficial is mean arterial pressure and heart rate which can be used to estimate additional diagnostic metrics such as intraocular pressure (IOP) and ocular perfusion pressure.

In step 770, derived metrics are estimated using as inputs the continuous (or near continuous) incremental data (step 740), patient parameters (step 750), and data provided by external devices (step 760). The strain may be volumetric or directional in various embodiments.

In step 780, continuous waveforms and trends data are displayed to the user. The data is displayed based on the continuous (or near continuous) incremental strain data (step 740) and estimated derived metrics (step 770).

Figure 8:
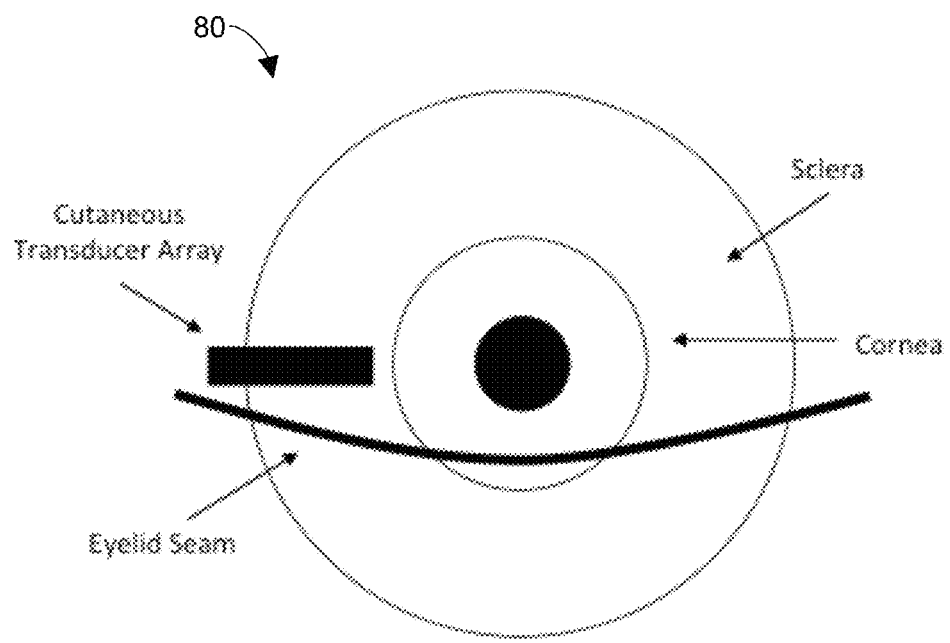
FIG. 8 is a schematic of a representative application of a transpalpebral transducer array to a patient's eyelid imaging the sclera according to an embodiment.

FIG. 8 is a schematic 80 of a representative application of a transpalpebral transducer array (e.g., array 10) to a patient's eyelid imaging the sclera. The device can be alternatively applied to imaging corneal strain via respective supra-corneal orientation of the array. The array is generally oriented superior and parallel to the eyelid seam, but need not be oriented along a principal circumferential direction, as discussed above. It is noted that the array will generally not be oriented perpendicular to the scleral (or corneal) radial axis, which will require incident beam and/or image correction using, e.g., beam steering in the case of ultrasound. As discussed above, intervening layers of tissue and fluid are discriminated from the target measured tissue using known idiosyncratic image characteristics of these layers.

Figure 9:
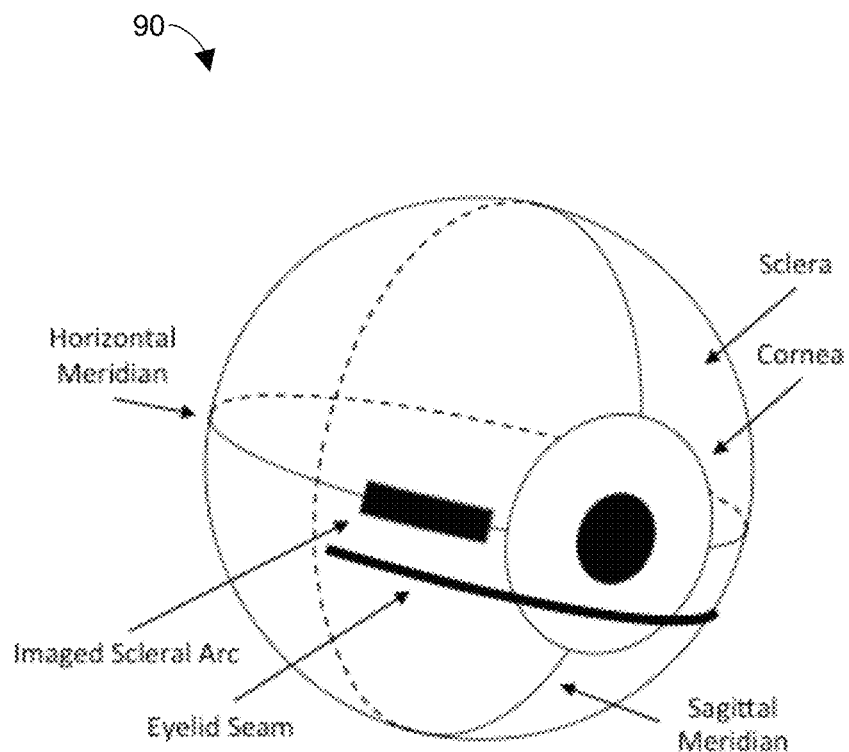
FIG. 9 is a schematic of an imaged tissue arc according to an embodiment.

FIG. 9 is a schematic 90 of the imaged tissue arc, in this case scleral, which again need not be oriented along a principal direction.

Some aspects of the above can include or modify some or all of clinical ultrasound systems and methods such as those described in Tang, J. and Liu, J., *Ultrasonic Measurements* of *Scleral Cross-Sectional Strains During Elevations of Intraocular Pressure: Method Validation and Initial Results in Posterior Porcine Sclera*, Journal of Biomechanical Engineering 2012; 134(9), 091007-1-091007-10. Additional aspects can include or modify some or all of the systems and methods described in Tanter, M. and Fink, M., *Ultrafast Imaging in Biomedical Ultrasound, IEEE* Transactions on Ultrasonics, Ferroelectrics, and Frequency Control 2014; 61(1):102-119. Additional aspects can include or modify some or all of the systems and methods described in Xie, T. et al., *Fiber-optic-bundle-based optical coherence tomography, Optics Letters* 2005; 30(14):1803-1805. Each of the foregoing references is incorporated herein by reference.

The present invention should not be considered limited to the particular embodiments described above, but rather should be understood to cover all aspects of the invention as fairly set out in the attached claims. Various modifications, equivalent processes, as well as numerous structures, materials and unforeseen technologies to which the present invention may be applicable, will be readily apparent to those skilled in the art to which the present invention is directed upon review of the present disclosure. The claims are intended to cover such modifications and equivalents.

What is claimed is:

1. An apparatus for noninvasive monitoring of an eye, the apparatus comprising:
    an adhesive support structure including:
        an elongated flexible backing layer having a first planar surface; and
        an adhesive layer disposed on said first planar surface of said elongated flexible backing layer; and
    an ultrasound device disposed in an aperture defined in said adhesive support structure, said ultrasound device including:
        a rigid or semi-rigid backing layer;
        a driver circuitry disposed on said rigid or semi-rigid backing layer;
        an array of ultrasound transducers in electrical communication with said driver circuitry; and
        a coupling gel disposed on said array of ultrasound transducers.

2. The apparatus of claim 1, further comprising an electronic cable connected to said driver circuitry, said electronic cable passing through a hole defined in said rigid of semi-rigid backing layer.

3. The apparatus of claim 2, wherein said electronic cable communicates control signals to said driver circuitry from an external microprocessor-based controller.

4. The apparatus of claim 1, wherein said ultrasound transducers are micromachined ultrasonic transducers.

5. The apparatus of claim 1, wherein said ultrasound device measures a strain of scleral or corneal tissue in said eye.

6. The apparatus of claim 1, wherein said aperture is disposed in a central region of said adhesive support structure.

7. An apparatus for noninvasive monitoring of an eye, the apparatus comprising:
    an adhesive support structure including:
        an elongated flexible backing layer having a first planar surface; and
        an adhesive layer disposed on said first planar surface of said elongated flexible backing layer; and
    an optical device disposed in an aperture defined in said adhesive support structure, said optical device including:
        a housing;
        a probe cable connected to a first wall of said housing, said probe cable including a fiber optic bundle;
        a collimating lens disposed proximal to said first wall of said housing, said collimating lens forming collimated electromagnetic (EM) waves from uncollimated EM waves passing through said collimating lens, said uncollimated EM waves transmitted by said fiber optic cable; and
        a focusing lens disposed proximal to a second wall of said housing, said focusing lens configured to focus said collimated EM waves at a target in said eye,
        wherein said probe cable, said collimating lens, and said focusing lens are disposed in said housing.

8. The apparatus of claim 7, further comprising a mirror arranged to direct said collimated EM waves to said focusing lens.

9. The apparatus of claim 7, wherein said uncollimated EM waves have a central wavelength of 1310 nm.

10. The apparatus of claim 7, wherein the focusing lens includes a liquid lens having a dynamic focal point and said probe cable includes an electronic cable to drive said liquid lens.

11. The apparatus of claim 7, wherein said uncollimated EM waves are generated by a broadband super luminescent diode.

12. The apparatus of claim 7, wherein said focusing lens is removable.

13. The apparatus of claim 7, wherein said fiber optic cable is disposed on a window in said housing, said window transparent to said uncollimated EM waves.

14. The apparatus of claim 1, wherein ultrasound device measures a strain of scleral or corneal tissue in said eye.

15. The apparatus of claim 7, wherein said aperture is disposed in a central region of said adhesive support structure.

16. A system for noninvasive monitoring of an eye, the system comprising:
    a transpalpebral probe assembly including:
        an adhesive support structure including:
            an elongated flexible backing layer having a first planar surface; and
            an adhesive layer disposed on said first planar surface of said elongated flexible backing layer;
        an ultrasound device disposed in an aperture defined in said adhesive support structure, said ultrasound device including:
            a rigid or semi-rigid backing layer;
            a driver circuitry disposed on said rigid or semi-rigid backing layer;
            an array of ultrasound transducers in electrical communication with said driver circuitry; and
            a coupling gel disposed on said array of ultrasound transducers;
    a microprocessor-based computer in communication with the assembly, the computer including:
        a probe driver complex including a driver logic to provide a control signal to said driver circuitry in said ultrasound device and analog-to-digital converters to transform an output of the ultrasound device to digital signals; and
        a processor in communication with the probe driver complex, the processor outputting a signal representing a transpalpebral acoustical image of a portion of a subject's eye based at least in part on the digital signals; and
    a display in communication with the computer, the display displaying the image.

17. A system for noninvasive monitoring of an eye, the system comprising:
an assembly including:
an adhesive support structure including:
an elongated flexible backing layer having a first planar surface; and
an adhesive layer disposed on said first planar surface of said elongated flexible backing layer;
an optical device disposed in an aperture defined in said adhesive support structure, said optical device including:
a housing;
a probe cable connected to a first wall of said housing, said probe cable including a fiber optic bundle;
a collimating lens disposed proximal to said first wall of said housing, said collimating lens forming collimated electromagnetic (EM) waves from uncollimated EM waves passing through said collimating lens, said uncollimated EM waves transmitted by said fiber optic cable; and;
a focusing lens disposed proximal to a second wall of said housing, said focusing lens configured to focus said collimated EM waves at a target in said eye,
wherein said probe cable, said collimating lens, and said focusing lens are disposed in said housing;
a broadband super luminescent diode coupled to said fiber optic cable, said diode generating said uncollimated EM waves;
a microprocessor-based computer in communication with the assembly and the light source, the computer including a processor to determine a scleral strain or a corneal strain of a subject and to generate an output signal representing a transpalpebral optical image of a portion of a subject's eye, the respective scleral or corneal strain and the output signal based at least in part on an output signal of the assembly; and
a display in communication with the computer, the display displaying the image.

* * * * *